United States Patent
Takayama

(10) Patent No.: US 6,674,889 B1
(45) Date of Patent: Jan. 6, 2004

(54) PATTERN INSPECTION METHOD AND PATTERN INSPECTION APPARATUS

(75) Inventor: Naohisa Takayama, Tokyo (JP)

(73) Assignee: NEC Corporation, Tokyo (JP)

( * ) Notice: Subject to any disclaimer, the term of this patent is extended or adjusted under 35 U.S.C. 154(b) by 612 days.

(21) Appl. No.: 09/597,701

(22) Filed: Jun. 19, 2000

(30) Foreign Application Priority Data

Jun. 17, 1999 (JP) ............................................ 11/171293

(51) Int. Cl.$^7$ ................................................. G06K 9/00
(52) U.S. Cl. ...................... 382/149; 382/147; 382/173; 348/130
(58) Field of Search ................................ 382/144, 147, 382/149, 218, 141, 145, 173, 209, 216; 356/237.3, 237.4, 237.5, 390, 394; 358/1.13; 430/5; 348/86, 87, 94, 95, 125, 126, 129, 130

(56) References Cited

U.S. PATENT DOCUMENTS

| | | | |
|---|---|---|---|
| 4,628,531 A | | 12/1986 | Okamoto et al. |
| 5,565,285 A | * | 10/1996 | Takekuma et al. ............. 430/5 |
| 5,577,171 A | * | 11/1996 | Arai et al. .................. 358/1.13 |
| 5,619,429 A | | 4/1997 | Aloni et al. |
| 5,777,901 A | * | 7/1998 | Berezin et al. ............... 716/19 |
| 5,900,941 A | * | 5/1999 | Matsuyama et al. ........ 356/394 |
| 6,064,484 A | * | 5/2000 | Kobayashi et al. .......... 356/390 |

FOREIGN PATENT DOCUMENTS

| | | |
|---|---|---|
| EP | 0 838 679 A2 | 4/1998 |
| JP | 1-305477 A | 12/1989 |
| JP | 4-365045 | 12/1992 |
| JP | 6-325162 A | 11/1994 |
| JP | 2776416 | 5/1998 |
| JP | 10-185531 | 7/1998 |

OTHER PUBLICATIONS

Patent Abstracts of Japan, vol. 014, No. 329, Jul. 16, 1990 (corresponds to JPA 2–108947, published Apr. 20, 1990).

Patent Abstracts of Japan, vol. 008, No. 257, Nov. 24, 1984 (corresponds to Ajpa 59–128419, published Jul. 24, 1984).

* cited by examiner

Primary Examiner—Bhavesh M. Mehta
Assistant Examiner—Ali Bayat
(74) Attorney, Agent, or Firm—Sughrue Mion, PLLC

(57) ABSTRACT

The present invention provides a pattern inspection apparatus whereby, even if a large number of defects are detected during inspection it is possible to continue inspection without interruption of the inspecting operation and the apparatus comprising optical means 4 and 5 for generating pattern image data from a pattern under test 9 held by the moving holding means 3, an image comparison sections 71 that compare the pattern under inspection with reference pattern image information so as to make a judgment as to whether or not a defect exists in the partial patterns under inspection, the image comparison sections 71 having a comparison pattern image information storage means 712, which stores comparison pattern image data for a partial pattern under inspection, reference pattern image information storage means 711 and/or 713 which store reference pattern image data corresponding to the partial patterns under inspection and an image processing means 715 that perform a comparison between the comparison pattern image data and the reference pattern image data so as to make a judgment as to whether or not there is a defect in the pattern under inspection. This apparatus 100 further having a defect information accumulation means 83 which sequentially stores defect information of a prescribed partial pattern under inspection in the respective inspection regions output by the image processing means 715 in the image comparison sections 71 and a reviewing means 8, which outputs defect information at a prescribed time.

29 Claims, 7 Drawing Sheets

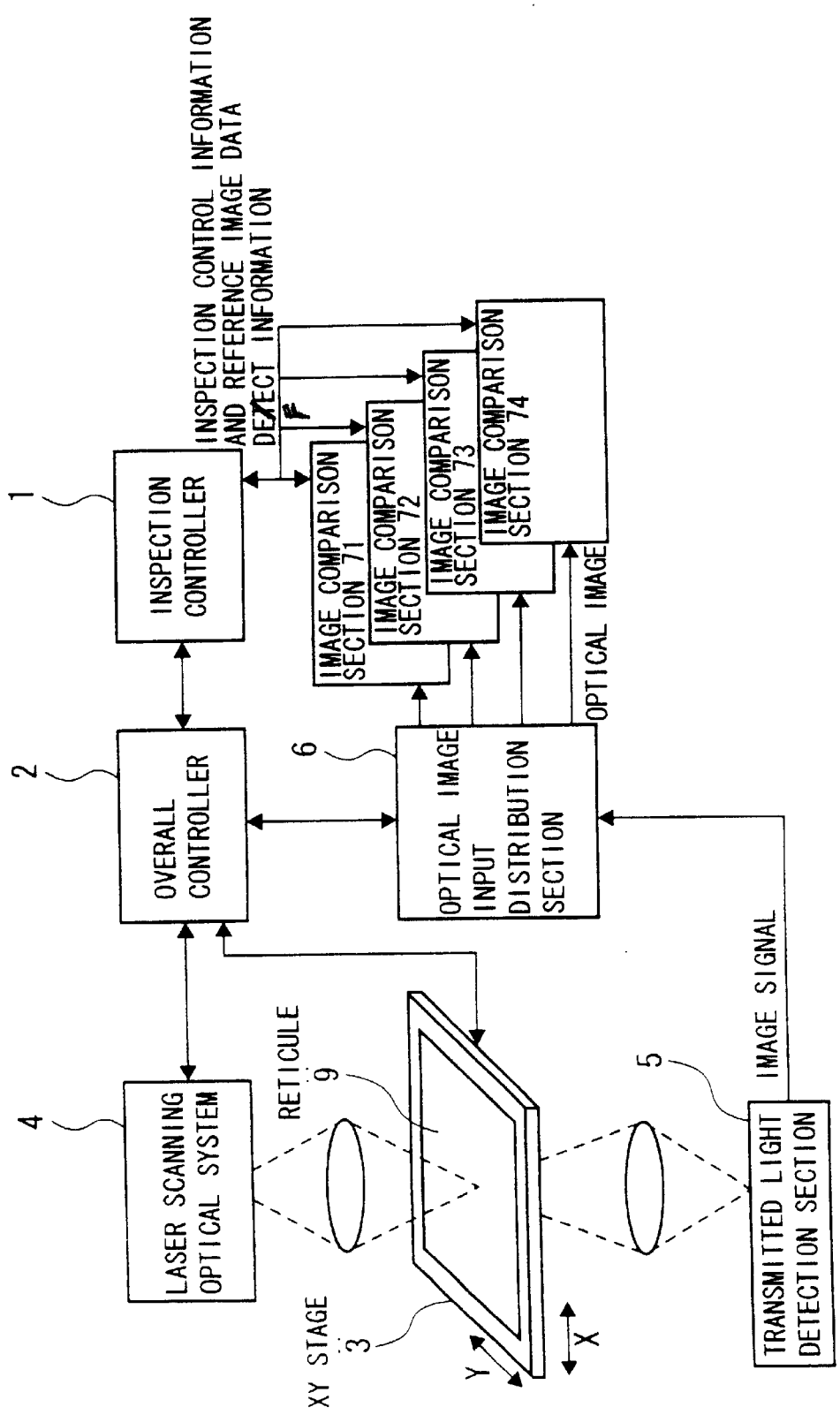

PATTERN INSPECTION METHOD AND PATTERN INSPECTION APPARATUS

BACKGROUND OF THE INVENTION

1. Field of the Invention

The present invention relates to a pattern inspection method and a pattern inspection apparatus, and more particularly to pattern inspection method capable of performing a review and analysis without interrupting an inspection operation for fault information with regard to a prescribed pattern, and to an associated pattern inspection apparatus.

2. Description of the Related Art

In the past, in the process of manufacturing a semiconductor device, many processes have been used to form a pattern of a specific shape in a specific member.

In each of these processes, to ensure that the desired pattern satisfies pre-established conditions, it is necessary that a master pattern be precisely formed.

For this reason, whether or not the master pattern is precisely formed greatly affects the quality and performance of the final semiconductor product, and also influences an improvement in yield.

A general example of such a master pattern is in an electron beam exposure method, in which a reticule is used onto which are formed a plurality of patterns used when forming a desired pattern on a wafer, in which precision in the patterns formed on the reticule is important.

The problems involved in an example of a method of inspecting the patterns formed in a reticule are described below.

Specifically, in an LSI manufacturing process (patterning), a reticule is used to form a prescribed pattern on a semiconductor made of silicon or the like. If there is a pattern defect in the reticule itself, the defective pattern will be transferred to a large number of wafers, causing the manufacture of a large number of defective LSI devices, thereby making inspection of the reticule very important.

Visual inspection methods for a reticule used in LSI manufacturing include the die-to-die inspection method, in which the same pattern at different locations on a reticule are compared, and the die-to-database inspection method, in which a comparison is made between a reticule pattern and image data used to form the reticule pattern.

The term die used herein is used to indicate a pattern area including a certain number of patterns as a group used as an unit of a pattern comparison inspection or an a detected image thereof, while the term database used herein refers with respect to an actual pattern image data detected with an optical system, but rather to image data based on coordinate data, such as a reference image synthesized from CAD data or the like, for example.

A reticule inspection apparatus of the past was disclosed, for example, in the Japanese Unexamined Patent Publication (KOKAI) No. 10-185531, in Japanese Patent No. 2776416, and in the Japanese Unexamined Patent Publication (KOKAI) No. 4-365045.

Specifically, a reticule inspection apparatus of the past was generally formed by an XY stage for setting the reticule, an imaging optical system for forming a photoimage of the pattern of the reticule set on the XY stage to serve as a comparison image, an image input section for acquiring a photoimage that is the comparison image from the imaging optical system, a data conversion section that converts image data used in describing the reticule, such as CAD data, to a reference image, an image comparison section for comparing the comparison photoimage with the reference image so as to detect defects in the pattern, and a controller to perform overall control of the apparatus.

A reticule inspection apparatus of the past moved the stage onto which was set a reticule, and acquired one frame of pattern on the reticule using an imaging optical system and image input section, and sent the acquired image to the image comparison section.

The reference image is converted beforehand by the data conversion section to a reference image from, for example, CAD data, and is sent to the image comparison section in synchronization with the image.

At the image comparison section, a comparison is made between the image and the reference image, so as to detect defects.

A frame used in the above-noted prior art example is the unit of image that can be processed by the image comparison section at one time.

Compared to the time for acquisition of an image by the imaging optics system and image input section, the time for transfer from the image input section to the image comparison section, the time for conversion of the image data, and the time for image processing to detect defects are significantly long, so that in a reticule inspection apparatus of the past, even if the next frame of image is acquired by the image input section, unless the series of processing for defect detection in the previous frame is completed, it is not possible to transfer the next frame of image, thereby resulting in a waiting time.

For this reason, the stage movement speed is made slow, thereby delaying the image acquisition time so as to achieve adjustment of timing, but this results in the lengthening of the overall inspection time.

In the above-noted the Japanese Unexamined Patent Publication (KOKAI) No. 10-185531, in the above-noted technical constitution, in order to improve defect detection precision and shorten detection time, a method of dividing a laser beam is used. In the above-noted Japanese Patent No. 2776416, for the same purpose, a simulation means is adopted, and a comparison is made between the results of the simulation and an actually measured pattern image. In the Japanese Unexamined Patent Publication (KOKAI) No. 4-365045, the method adopted is that of using CAD data as reference data, and the above-noted problems remain basically unsolved.

Given the above, the inventors, in the Japanese Unexamined Patent Publication (KOKAI) No. 10-115049, proposed an improved technology as shown in FIG. 7.

Specifically, when performing pattern inspection, inspection in each region is done by first moving an XY stage 3, onto which is set a reticule 9, to an inspection staring position.

Next, the XY stage 3 is fed in the X direction at a constant speed, as a laser scanning optical system scans in the Y direction each time a laser interferometer detects movement by a constant pitch, the transmitted light being detected by a transmitted light detection section 5, and an optical image input distribution section 6 acquiring a two-dimensional image for each frame.

The acquired optical images are synthesized by image comparison sections 71 to 74 for each frame separately, a comparison is made with a reference image, and defect detection is performed. The term frame used herein refers to the image that can be processed at one time by the image comparison section.

In FIG. 7, the reference numeral 1 denotes a scanning controller, and 2 is an overall controller.

In a method of inspection employed with this type of inspection apparatus, division is made into a plurality of overlapping inspection regions with their long dimensions in the X direction, for example, as shown in FIG. 3, scanning being sequentially performed for each region, after which the defects for each region are combined so as to perform defect detection for the overall reticle.

In the above-noted method, although the problems with the prior art are significantly improved upon, there is still the problem in the case in which a large number of defects are detected in each inspection region, in which case a large amount of time is required by the controller in order to extract defect information from each channel, thereby causing a waiting time to occur before image acquisition for the next inspection region, which meant that the problem of the overall inspection requiring a long time remained not fully solved.

Additionally, in the case in which defects detected during inspection are reviewed in real time, it is necessary to interrupt inspection in order to search for defect images stored in the controller, thereby leaving the problem that the overall inspection time is long.

Accordingly, it is an object of the present invention, in order to improve on the above-noted drawbacks in the prior art, to provide a pattern inspection method whereby, even if a large number of defects are detected during inspection and a review is to be made of defects in real time, it is possible to continue inspection without interruption, thereby providing an improvement in productivity. It is a further object of the present invention to provide a pattern inspection apparatus associated with the above-noted pattern inspection method.

SUMMARY OF THE INVENTION

In order to achieve the above-noted objects, the present invention has the following basic technical constitution.

Specifically, a first aspect of the present invention is a pattern inspection method which, in detecting defects in various patterns used in manufacturing a semiconductor device, has a first step of dividing a pattern under inspection into a pre-established number of regions and sequentially acquiring, via an optical means, image information with regard to partial patterns under inspection in each region, a second step of storing the image information with regard to the partial pattern under inspection acquired by the first step into a comparison pattern image information storage means provided in each of a pre-established plurality of image comparison sections, respectively, a third step of, in image processing means provided in each individual image comparison section, performing a comparison between the image information with regard to the partial patterns under inspection stored in the comparison pattern image information storage means and reference pattern image information (reference image information) corresponding to the partial pattern under inspection in the divided regions, which is stored beforehand in a reference pattern image information storage means provided in the image comparison sections, a fourth step of, in the case in which defect information exists with regard to a partial pattern under inspection, storing the defect information into a defect information storage means provided in a review controller, and a fifth step of outputting the defect information with regard to partial patterns under inspection for a prescribed divided region stored in the defect information storage means in a prescribed format or at a prescribed time.

A second aspect of the present invention is a pattern inspection apparatus for detecting defects in various patterns used in manufacturing a semiconductor device, this apparatus having a moving holding means for holding and moving in a prescribed direction a pattern holding member that holds a pattern under inspection, an optical means for generating pattern image data of a partial pattern under test from a pattern under test held by the moving holding means for every predetermined divided regions of the pattern under inspection, a plurality of image comparison sections that compare the individual partial patterns under inspection of the pattern under inspection with prescribed reference pattern image information, and make a judgment as to whether or not a defect exists in the partial patterns under inspection, each the image comparison sections minimally comprising a comparison pattern image information storage means which stores comparison pattern image data for a partial pattern under inspection corresponding to a specific inspection divided region, a reference pattern image information storage means which stores reference pattern image data corresponding to each of the partial patterns under inspection, and an image processing means that performs a comparison between the comparison pattern image data stored in the comparison pattern image information storage means and the reference pattern image data stored in the reference pattern image information storage means, and makes a judgment as to whether or not there is a defect in the pattern under inspection, a defect information accumulation means, which sequentially stores defect information in a prescribed partial pattern under inspection output by the image processing means in each the image comparison sections, a reviewing means, which outputs defect information with regard to each of the partial patterns under inspection stored in the defect information accumulation means with a prescribed format or at a prescribed time, and a central control means which performs appropriate overall control of the above-noted means.

By adopting the above-noted technical constitutions, even in the case in which a large number of defects are detected or even in the case in which defect reviewing is done in real time, a pattern inspection apparatus and pattern inspection method according to the present invention, by a simple addition to a precision visual reticle inspection apparatus for LSI device manufacturing, enable to perform continuous, uninterrupted inspection, thereby improving the productivity of the pattern inspection process.

Specifically, the review controller performs real-time collection, accumulation, and editing of defect information (including defect images) from each image comparison section, using dedicated lines, and searches and displays defect images on demand.

By doing the above in the present invention, because the review controller performs independent collection, accumulation, and editing of defect information detected for each channel, even if many defects are detected or if review is performed during the inspection process, it is not necessary to interrupt the inspection operation, thereby shortening the inspection time.

Additionally, because there is an existing database of past defect information in the review controller, it is possible to perform analysis of process problems and classification of defects caused by exposuring simulation.

BRIEF DESCRIPTIONS OF THE DRAWINGS

FIG. 7 is a block diagram showing an example of a pattern inspection apparatus associated with a pattern inspection apparatus of the present invention.

DETAILED DESCRIPTION OF THE PREFERRED EMBODIMENTS

Figure 1:
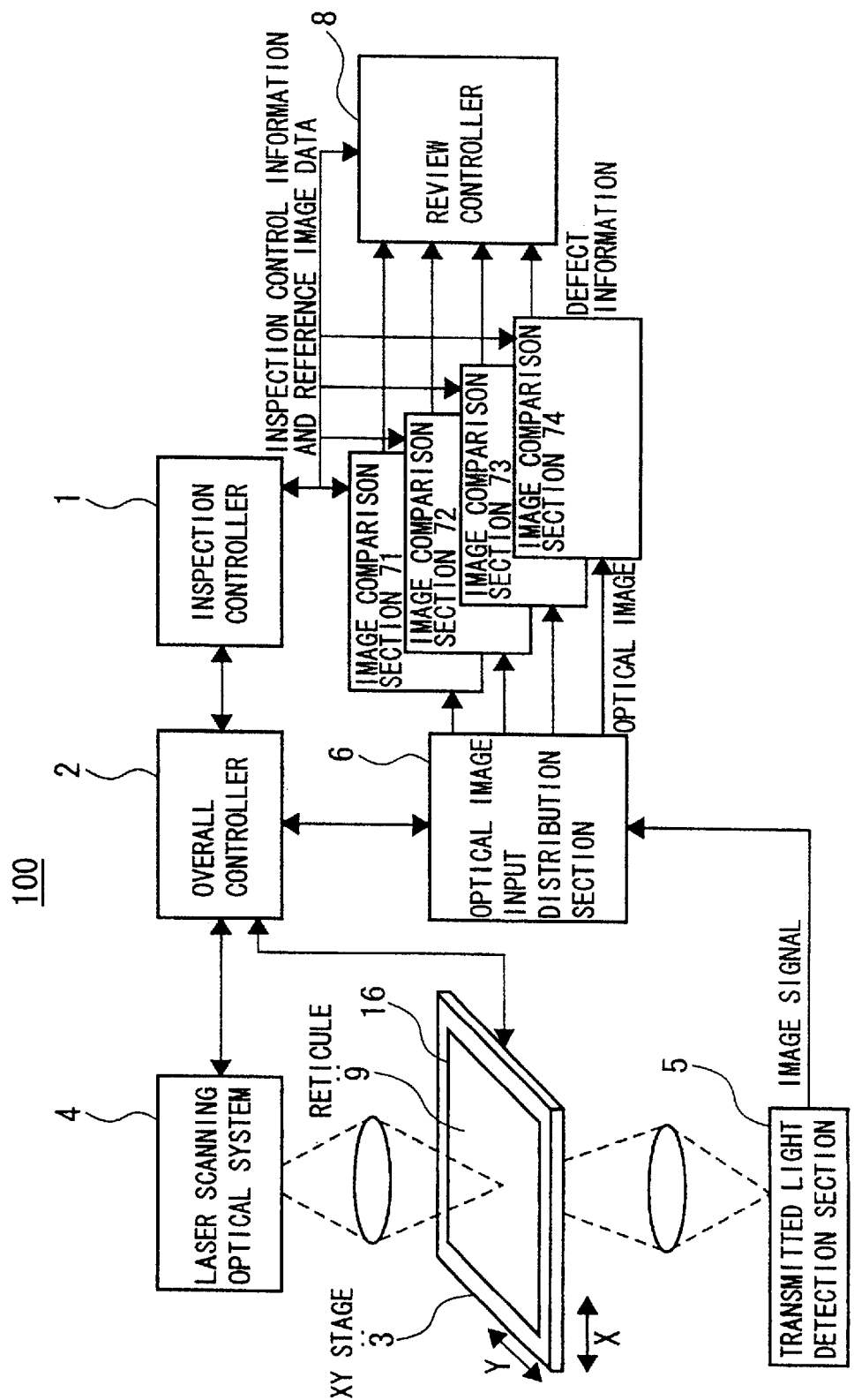
FIG. 1 is a block diagram illustrating the configuration of an example of a pattern inspection apparatus according to the present invention.

Embodiments of a pattern inspection method and a pattern inspection apparatus according to the present invention are described in detail below, with references made to relevant accompanying Specifically, FIG. 1 is a block diagram showing an example of a pattern inspection apparatus 100 according to the present invention. This inspection apparatus 100 has a moving holding means 3 for holding and moving in a prescribed direction a pattern holding member 16 that holds a pattern under inspection 9, optical means 4 and 5 for generating pattern image data from a pattern under test held by the moving holding means 3 for prescribed each one of the divided region of the pattern under inspection 9, and a plurality of image comparison sections 71 to 74 that compare the individual partial patterns under inspection of the pattern under inspection with prescribed reference pattern image information, and make a judgment as to whether or not a defect exists in the partial patterns under inspection. Each of the image comparison sections 71 to 74 minimally has a comparison pattern image information storage means 712, 722, 732, and 742, which stores comparison pattern image data for a partial pattern under inspection corresponding to a specific divided inspection region, reference pattern image information storage means 711, 721, 731, and 741 or 713, 723, 733, and 743, which store reference pattern image data corresponding to each of the partial patterns under inspection, and image processing means 715, 725, 735, and 745 that perform a comparison between the comparison pattern image data stored in the comparison pattern image information storage means and the reference pattern image data stored in the reference pattern image information storage means, and make a judgment as to whether or not there is a defect in the pattern under inspection. This pattern inspection apparatus 100 further has a defect information accumulation means 83 which sequentially stores defect information of a prescribed partial pattern under inspection in the respective inspection regions output by the image processing means 715, 725, 735, and 745 in each of the image comparison sections 71 to 74, a reviewing means 8, which outputs defect information with regard to each of the partial patterns under inspection stored in the defect information accumulation means 83 with a prescribed format or at a prescribed time, and a central control means 2 which performs appropriate overall control of the above-noted means.

The pattern under inspection in the present invention, is not particularly restricted, but it is desirable that this pattern be a reticule pattern formed on a reticule.

In the present invention, the pattern holding member is not particularly restricted, and can be an arbitrary member, as long as it is frame-like member that can hold the reticule with good stability.

It is desirable that the pattern moving holding means used in the present invention be, for example, an XY stage.

Additionally, the optical image reading means in the present invention is not particularly restricted, and can be a system in which a laser beam is shone onto the pattern, the light transmitted there through being used to reproduce the pattern image information.

In the specific example shown in FIG. 1, the example is that of an optical system formed by a laser scanning optical section 4 and a transmitted light detection section 5, with details of lens system disposed between the laser scanning optical section 4 and the transmitted light detection section 5 being omitted herein.

In the imaging optics 4 and 5, for example, a laser beam is output from the laser scanning optical section 4, which is caused to scan the surface of a reticule mounted on the XY stage 3 in the Y direction, the XY stage being moved in the X direction, which is perpendicular to the Y direction, the laser beam passing through the pattern, which in this case is the reticule, and the thus transmitted light being detected by the transmitted light detection section 5, the formed image pattern being sent to the optical image input distribution section 6

Figure 3:
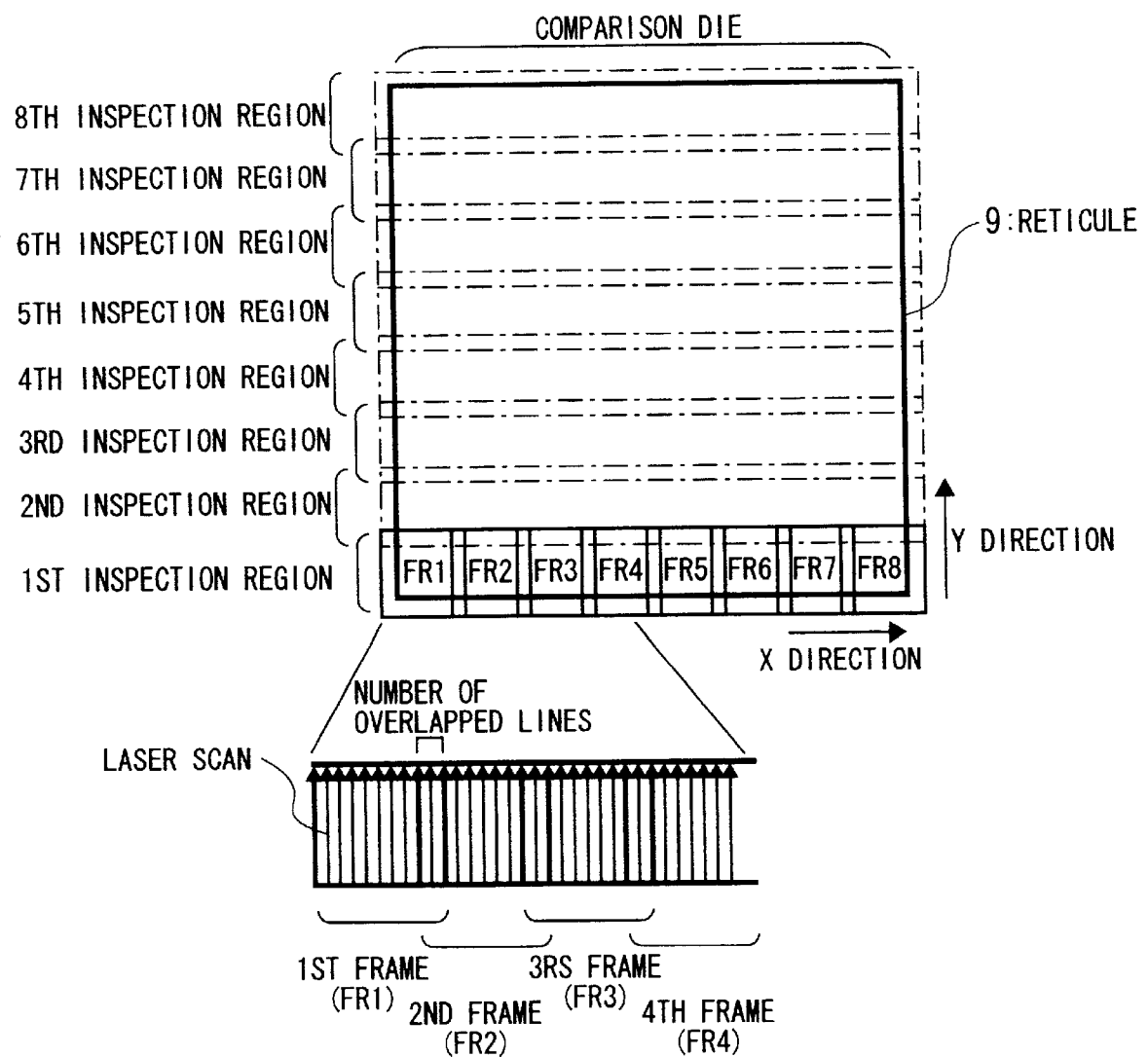
FIG. 3 is a drawing illustrating a pattern inspection procedure in an example of a pattern inspection apparatus according to the present invention.

In the above-noted system of the present invention, when one pattern image is acquired, as shown in FIG. 3, it is desirable that execution be done a prescribed divided region as a unit inspection area, formed by finely dividing each one of the inspecting area, and these being prescribed divided regions called frames.

In the present invention, a two-dimensional image pattern from frame 1 (FR1) to frame N (FRN)) for each frame (pattern under inspection) region is acquired and sent to the optical image input distribution section 6, after which the pattern image data is sequentially sent to the plurality of image comparison sections 71 to 74

In the present invention, specifically, for example, if the number of divided regions (frames) in one inspection area is set at 8, and the number of image comparison sections is set at 4, as illustrated in the drawing, one image comparison section is overwritten by a new partial pattern under inspection with every time four times the operation time for acquiring a partial pattern under inspection elapses.

Stated differently, this time period can be used for detecting the presence of defect information with regard to the partial pattern under inspection.

That is, in the present invention, it is desirable that the prescribed number of the image comparison sections 71 to 74 be set as a number that is smaller than the number of divided regions of an inspection area with regard to the partial pattern under inspection.

Specifically, in the above-noted example of the present invention, each of the comparison pattern image information storage means 712, 722, 732, and 742 provided in each one of the image comparison sections 71 to 74 stores pattern image information of partial pattern under inspection disposed in each prescribed divided region that is measured in real time, as comparison pattern image information.

In an example of a pattern inspection apparatus according to the present invention, the above-noted partial pattern under inspection sent to the image comparison sections 71 to 74 in real time and the reference pattern image information to be taken as a reference can be, for example, a data base including comprising a digital image database that is generated at a time when the pattern under inspection is formed, for example, from CAD data or the like.

More specifically, in the case in which die-to database comparison is used, it is desirable that data corresponding to partial patterns under inspection selected from the digital image database is stored into reference pattern image information storage means 713, 723, 733, and 743 either synchronized with or before the timing of the separate transmission of data regarding the comparison pattern image information via the optical image input distribution section 6 to each of the image comparison sections 71 to 74.

In the case of the die-to-die pattern inspection, a pattern as used for the reference pattern image information is a pattern having substantially the same configuration as the pattern under inspection, and this being pattern image data obtained from a reference pattern which is held in a pattern holding member which is identical to a pattern holding member on which the pattern under inspection is formed.

Figure 5:
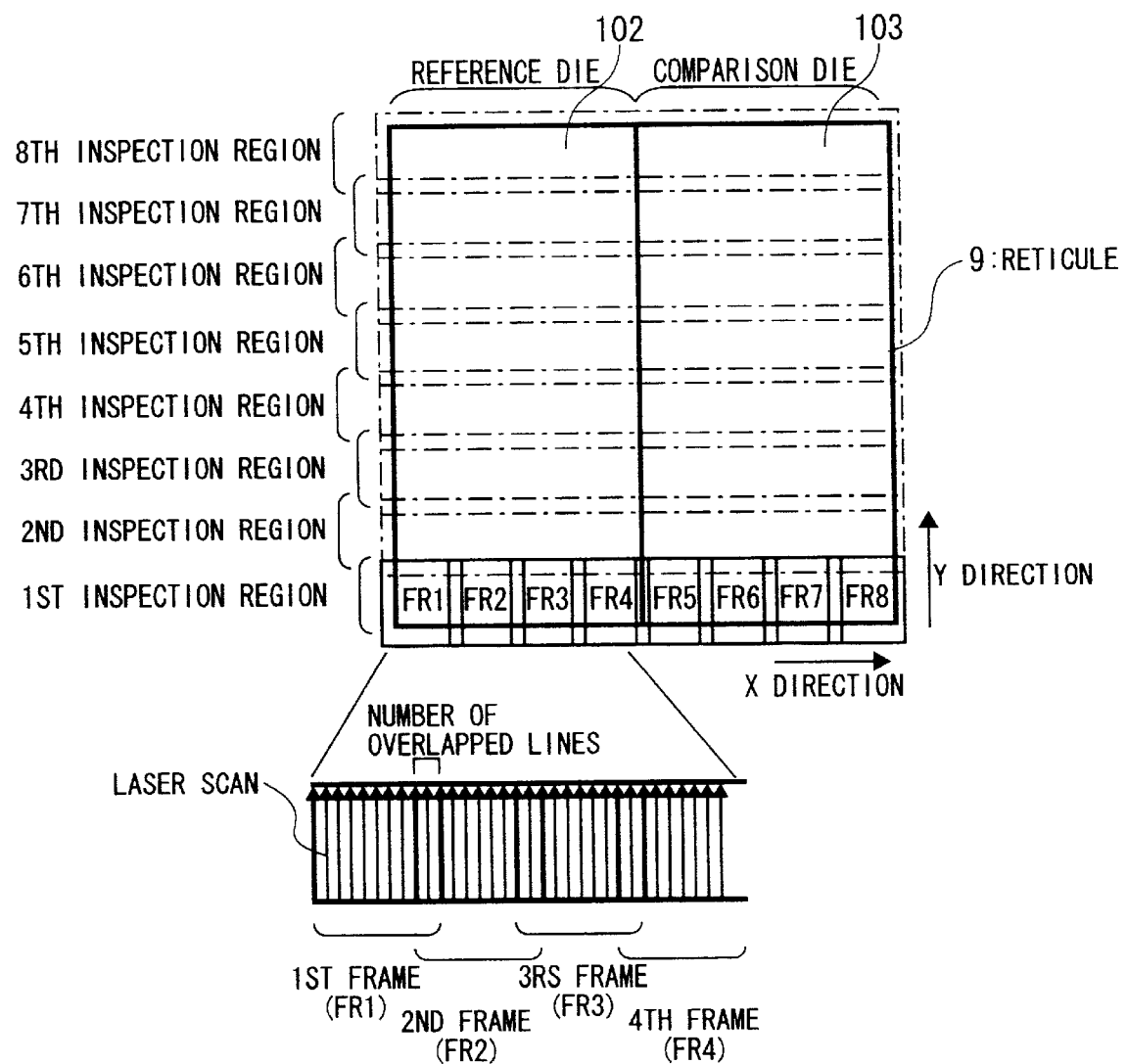
FIG. 5 is a drawing illustrating a pattern inspection procedure in another example of a pattern inspection apparatus according to the present invention.

That is, for example, as shown in FIG. 5, the reticule 9, which is the pattern under inspection, is divided into two in the vertical direction, the first region 102 being taken as the reference die, i.e., the region for forming the reference pattern to be used as reference data for the pattern under inspection, an the second region 103 being taken as the comparison die for formation of the pattern under inspection.

The overall reticle 9 is divided into a plurality of inspection areas (8 in this embodiment) in the horizontal direction, each inspection area being sub-divided into 4 divided regions that are included in the reference die 102, these being 4 frames (FR1 to FR4), simultaneously with which the overall inspection region is sub-divided into 4 divided regions that are included in the comparison die 103, these being 4 frames (FR5 to FR8), thereby forming each of the prescribed inspection patterns.

The first divided region (FR1) and the fifth divided region (FR5) have substantially the same shaped patterns formed therein, as do the second divided region (FR2) and the sixth divided region (FR6), the third divided region (FR3) and the seventh divided region (FR7), and the fourth divided region (FR4) and the eight divided region (FR8).

Pattern are formed in other inspection regions in the same manner.

The operation of dividing and sub-dividing the above-noted inspection regions into a plurality of frames can, of course, be executed by software.

In this embodiment, when inspection a partial pattern under inspection disposed in a comparison die, first, in the case of inspecting the partial pattern under inspection disposed in the fifth frame (FR5) of the comparison die, first the pattern image data of the first frame FR1 including the reference pattern image corresponding to this partial pattern under inspection is acquired and stored into the reference pattern image information storage means 711 provided in the image comparison section 71.

Then, after acquiring pattern image data regarding the partial pattern under inspection disposed in the fifth frame (FR5), this pattern image data is stored into the comparison pattern image information storage means 712 provided in the image comparison section 71.

In the same manner, in the case of inspecting a partial pattern under inspection in the sixth frame FR6 of the comparison die, the pattern image data of the second frame FR2 including the reference pattern corresponding to this partial pattern under inspection is first acquired and then stored into the reference pattern image information storage means 721 provided in the comparison section 72.

The, after acquiring pattern image information regarding the partial pattern under inspection disposed in the sixth frame FR6, this pattern image data is stored into the comparison pattern image information storage means 722 provided in the image comparison section 72.

Thereafter, in the same manner, pattern image data for all the partial patterns under inspection of the first inspection region and pattern image data for the corresponding reference patterns are sent to the image comparison sections, after which the process moves on to the second inspection region, for which the above-noted operations are executed.

Thus, in the present invention, the reference pattern image information storage means includes pattern image information derived from a pattern having substantially the same shape as the pattern under inspection, and which is obtained from a reference pattern formed on the same pattern holding member as is formed the pattern under inspection.

In this embodiment, it is desirable that the reference pattern that provides the reference pattern image information be disposed near the partial pattern under inspection on the pattern holding member.

Additionally, it is desirable in this embodiment that the reference pattern be configured so said to detect a pattern in the substantially same range as the partial pattern under inspection in one inspection step in the partial pattern under inspection as a reference pattern image.

As is clear from the above description, it is desirable that the operation of detecting the reference pattern image be executed at a prescribed amount of timing before the operation of pattern image detection of the corresponding partial pattern under inspection.

In this embodiment, it is desirable that, when reading a partial pattern under inspection for each frame, the reading be done so that there is a prescribed range of mutual overlap, which includes the edge parts of adjacent divided regions.

In the present invention, in each of the image processing sections 715, 725, 735, and 745 provided in each of the image comparison sections, a real-time comparison is made between pattern image data of partial patterns under inspection stored sequentially in the comparison pattern image information storage means 712, 722, 732, and 742 of the image comparison sections and reference pattern image data corresponding to each partial pattern under inspection stored in the reference pattern image information storage means 713, 723, 733, and 743 in of the image processing sections 715, 725, 735, and 745, and a judgment is made as to whether or not defect information is included in the partial pattern under inspection. If the result of this judgment is that defect information is included in the partial pattern under inspection, that information is sent to a defect information accumulation section 83 provided in the review controller 83 and stored therein.

There is no particular restriction with regard to the algorithm used in this embodiment to execute a judgment as to whether or not defect information is included in the partial pattern under inspection in each of the image processing sections 715, 725, 735, and 745, and this can be implemented using a known algorithm of the past.

The review controller 8 in this embodiment of the present invention further preferably includes a database system 85 that minimally stores digital image data, pattern manufacturing process data, and past defect judgment results, these various stored data being appropriately used to output only the most recent pattern defect information detection results, but also information related to the processing of the most recent pattern defect information thereby providing guidelines to an operator with regard to handling of this partial pattern under inspection defect information.

For example, in addition to clearly identifying from the defect information problems in the pattern manufacturing process and problems with manufacturing equipment, it is possible, by referring to the frequency of occurrence of defect information and the pattern of occurrence, it is possible to make a judgment as to whether or not the defect information can be ignored, and possible, when the same type of defect is repeated, to obtain information as to what type of countermeasure can be taken.

Additionally, in the present invention it is preferable that, defect information output from each of the image processing sections be temporarily stored in the defect memories 716, 726, 736, and 746 provided in each one of the image processing sections 715, 725, 735, and 745 formed in each one of the comparison sections 71 to 74, respectively.

As is clear from the foregoing description of the configuration of a pattern inspection apparatus according to the present invention, a method for pattern inspection according to the present invention has the following constitution.

Specifically, a method for pattern inspection according to the present invention, when detecting pattern defects, has a first step of dividing the pattern under inspection into a pre-established number of regions (frames FR1 to FR8) and sequentially acquiring, via an optical means 4 and 5, image information with regard to partial patterns under inspection in each region, a second step of storing the image information with regard to the partial pattern under inspection acquired by step 1 into comparison pattern information storage means 712, 722, 732, and 742 provided in each of a pre-established plurality of image comparison sections 71 and 74, a third step of, in the image processing means 715, 725, 735, and 745 provided in each individual image comparison section 71 to 74, performing a comparison between the image information with regard to the partial patterns under inspection stored in the comparison pattern image information storage means 712, 722, 732, and 742 and reference pattern image information (reference image information) corresponding to the partial pattern under inspection in the divided regions, which is stored beforehand in reference pattern image information storage means 713, 723, 733, and 743 provided in the image comparison sections 71 to 74, a fourth step of, in the case in which defect information exists with regard to a partial pattern under inspection, stores the defect information into a defect information storage means provided in a review controller 8, and a fifth step of outputting the defect information with regard to partial patterns under inspection for a prescribed divided region stored in the defect information accumulation means in a prescribed format or at a prescribed time.

In the present invention, it is desirable that the prescribed number of the image comparison sections be set as a number that is smaller than the number of divided regions with regard to the partial pattern under inspection.

The reference pattern image information in the present invention is preferably a database that is made of digital image data generated at the time of forming the pattern.

Additionally, in a method for pattern inspection according to the present invention, it is desirable that the pattern image information be derived from a pattern having substantially the same shape as the pattern under inspection, and which is obtained from a reference pattern formed on the same pattern holding member as is formed the pattern under inspection.

In the above case, it is desirable that the pattern that provides the reference pattern image information be disposed near the partial pattern under inspection on the pattern holding member. Additionally, it is desirable in this embodiment that the reference pattern be configured so said to detect a pattern in the substantially same range as the partial pattern under inspection in one inspection step in the partial pattern under inspection as a reference pattern image.

Additionally, in the above case it is desirable that the operation of detecting the reference pattern image be executed at a prescribed amount of time before the operation of pattern image detection of the corresponding partial pattern under inspection.

In another example of a method for pattern inspection according to the present invention, it is desirable that the reference pattern image information storage means minimally has stored therein either reference pattern image information from a database corresponding to a pattern under inspection selected from a digital image database, or reference pattern image information that is image data obtained via the optical means from the reference pattern held in the pattern holding member.

In a pattern inspection method according to the present invention, of the calculation results obtained by the image processing sections provided in the image comparison sections, image data indicating defects in a prescribed pattern under inspection is all sequentially stored into a defect information accumulation means 83 provided in the review controller 8.

Additionally, because it is possible, without any restrictions on the operation conditions in any of the above-noted first to fourth steps, to it is possible to achieve a prominent improvement in the efficiency of pattern inspection.

A detailed embodiment of the present invention is described below, with references made to relevant accompanying drawings.

Referring to FIG. 1, the first embodiment of the present invention is shown as a reticule inspection apparatus 100.

This apparatus has an XY stage 3 onto which is set a reticule 9, a laser scanning optical apparatus 4, which scans a laser beam in the Y direction and collects transmitted light, a transmitted light detection section 5 for detecting collected transmitted light, an optical image input distribution section 6, which obtains an image signal from the transmitted light detection section 5, generates an optical image, and distributes this to each image comparison section 71 to 74, an overall controller 2 that performs control of the XY stage 3 and the laser scanning optical apparatus 4, image comparison sections 71 to 74 which compare a reference image synthesized from intermediate data with an optical image so as to detect a pattern defect, and a review controller 8, which collects, accumulates, and edit said defect information (including defect images) from each image comparison section 71 to 74 in real time and, in response to a request, searches and displays defect images.

Figure 2:
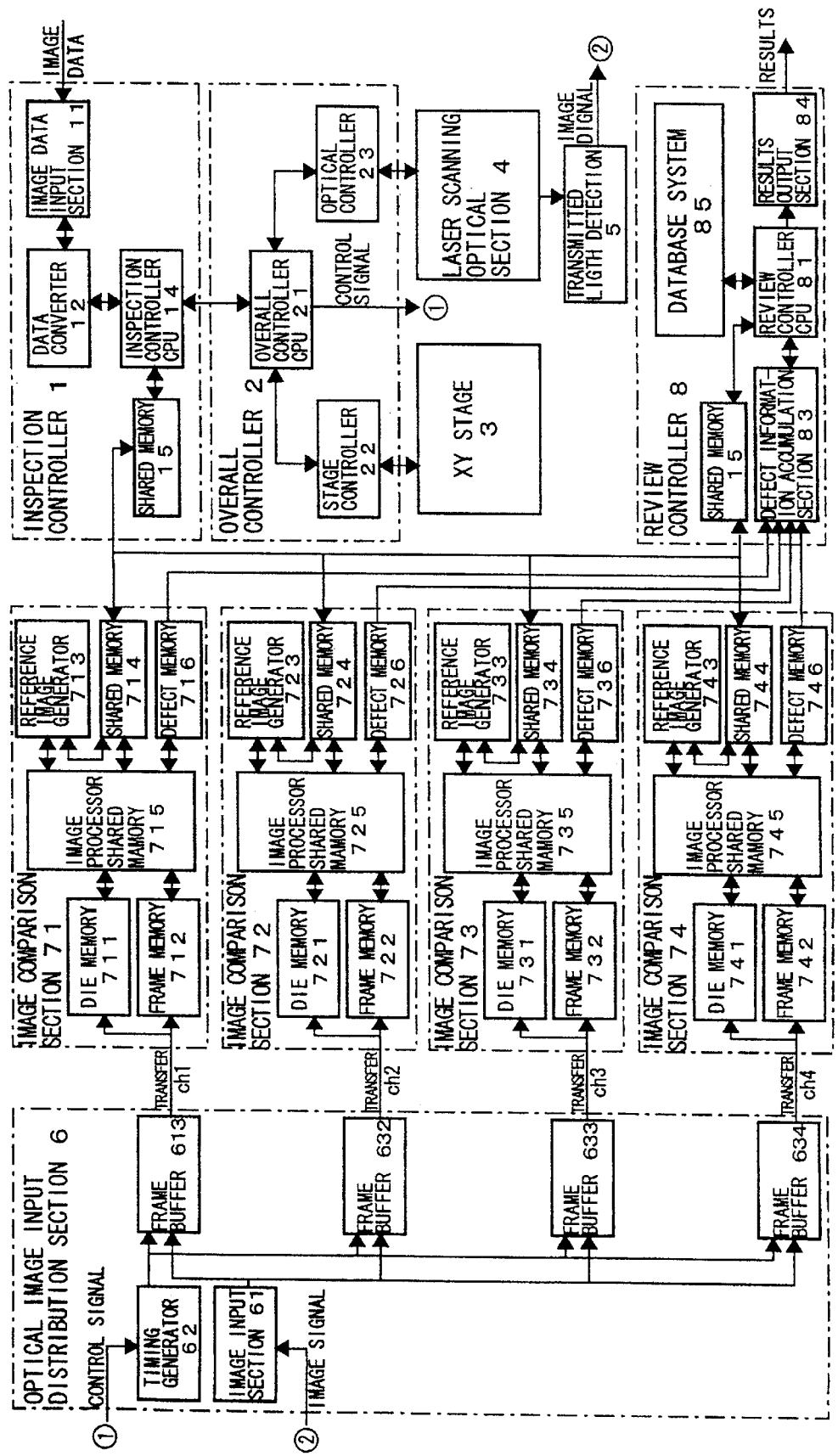
FIG. 2 is a block diagram illustrating a specific configuration example of an image comparison section and review controller used in an example of a pattern inspection apparatus according to the present invention.

Referring to FIG. 2, we see the detailed configuration of the parts shown in FIG. 1.

In the above-noted embodiment, it is possible to configure the laser scanning optical apparatus 4 an the transmitted light detection section 5 using a mercury lamp and a CCD line sensor.

Figure 4:
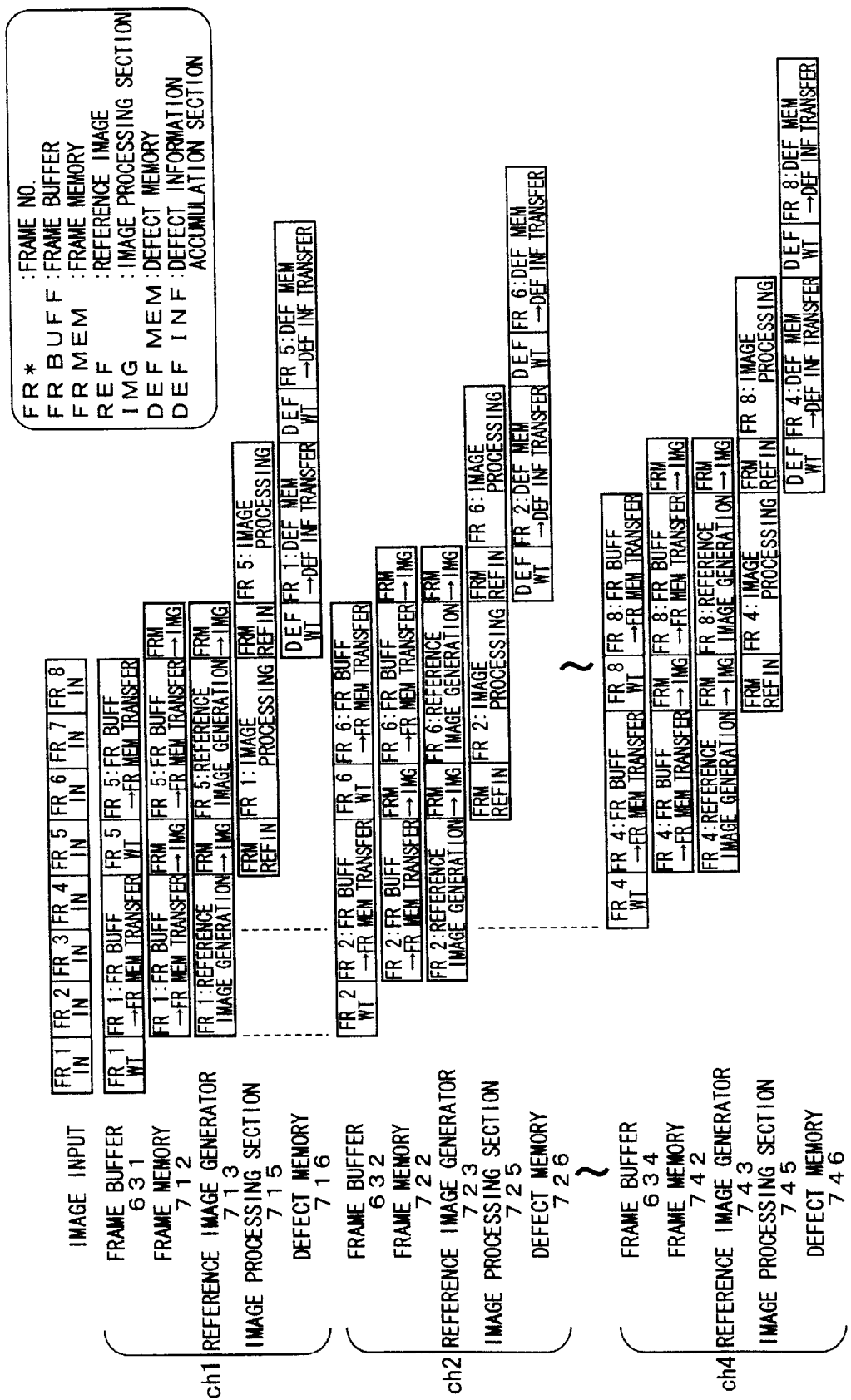
FIG. 4 is a timing diagram of inspection performed by an example of a pattern inspection apparatus according to the present invention.

The die-to-database inspection operation of FIG. 3 is described below, with reference made to the system block diagram of FIG. 2 and the timing diagram of FIG. 4.

In the inspection pre-processing, the descriptive data used to describe the reticule 9 to be inspected is acquired by the described data input section 11, and this is converted for each frame into reference image intermediate data by the data converter 12, this being then sent to each image comparison section 71 to 74 via a common memory 15.

When the inspection is started, the overall control CPU 21 sends a command to the stage controller 22 and the optical system controller 23, and acquisition of optical images begins.

For example, in order to inspect an inspection images from the first frame to the eight image of the first inspection region, first the XY stage 3 is caused to move at a fixed speed in the X direction, and for fixed pitch of movement of in the X direction, the laser light is scanned in the Y direction by the laser scanning optical apparatus 4 and the transmitted light is detected by the transmitted light detection section 5, the detected image signals being formed into a two-dimensional image by the image input section 61 provided in the optical image input distribution section 6.

Then, images for the second through the eight frames are sequentially acquired, so as to obtain the optical images for all eight frames of the first inspection region.

To acquire the second inspection region, after causing the XY stage 3 to move a fixed pitch in the Y direction, the XY stage 3 is moved in the opposite direction (-X direction) at a constant speed and the same type of operation is performed. This series of operations is repeated, so as to perform image acquisition and inspection of the entire reticule.

The two-dimensional optical image formed by the image input section 61 is divided into individual frames by control of the timing generation section 62, and written into individual frame buffers 631 to 634.

The timing generator 62 has set in it by the overall control CPU 21 the number of scan lines for one frame and the number of overlapping lines between frames, an image acquisition start signal from the overall control CPU 21 causes image acquisition to begin, the number of lines input being monitored and the write frame buffer being selected.

When this done, it is desirable that the number of overlapped lines between frames is written into two frame buffers.

The reason that a number of overlapped lines is needed is that, because adjacent frames are processed at an image comparison section, if a defect exists at precisely the divide between two frames, surrounding information will be lost and it will be impossible to distinguish a defect.

The first captured frame (FR1) is written into the frame buffer 631 for channel 1 transfer, and simultaneously with completion of transfer into the frame memory 712 of the image comparison section 71 begins.

The image input section 61 acquires the next frame (FR2) without any waiting time, and performs writing into the frame buffer 632 for channel 2 transfer, after which the frame buffers are sequentially switched so as to write into frame buffers up to the frame buffer 634.

When writing into the frame buffer 634 is completed, return is made to the frame buffer 631, from which point cyclic image acquisition, writing, and transfer are performed.

Therefore, the time between the writing into one buffer and the time at which that frame is again written (overwritten) corresponds to the time form processing the image of one frame (cycle time), so that it is necessary to complete processing by each image comparison section during the cycle time.

The reference image that is compared is generated in real time for each frame comparison processing at the reference pattern image information storage means. As described above, the inspection processing is processing in which the reference pattern image data is converted to intermediate data that is easily expandable from descriptive image data by the data converter 12, this being transferred, via the shared memory 15, to the shared memory of each image comparison section.

The processing thereafter is described with regard to the image comparison section 71, the processing by the other image comparison sections 72 to 74 being performed asynchronously in the same manner.

When the inspection begins, at the reference pattern image information storage means 713 the reference image intermediate data for the first frame (FR1) is extracted from the shared memory 714, the reference image data is expanded to a bit map, an defocusing processing is applied to generate a reference image.

The defocusing processing is required in order to approximate the image optically obtained from the object of comparison using the reference image.

When the optical image of the first frame (FR1) is transferred to the frame memory 712, the reference image is synchronized to the optical image and transferred from the reference image generation section 713 to the image processing section 715.

When the transfer of the reference image to the image processing section 715 is completed, the reference pattern image information storage means 713 immediately extracts the reference image intermediate data of the next frame (FR5) from the shared memory 714, and generates a reference image. That is, at the image generation section 713, the reference image for the next frame to be compared is always performed beforehand, so that there is no waiting time at the image processing section 715.

At the image processing section 715, comparison pattern image information which is an optical image transferred to the frame memory 715 is compared with a reference image generated at the reference pattern image information storage means 713 are compared in units of frames to detect defects and, if a defect is detected, the defect information is written into the defect memory 716.

When information is written, the defect memory 716 transfers defect information to the defect information accumulation section 83 of the review controller 8 in real time.

When the above is done, because the route of writing reference pattern data and inspection control information, that is the route from the shared memory 15 to the shared memory 14, is totally independent from the route of sending the defect information, this being from the defect memory 716 to the defect information accumulation section 83, it is possible to transmit defect information without interrupting the inspection process.

A review control CPU 81 provided in the review controller 8 collects defect information of each of the image comparison sections 71 to 74 that was accumulated in the defect information accumulation section 83, taking into consideration the number of overlap lines between frames, and generates defect information for the overall reticule.

Even during an inspection, in response to a request from an operator, a result outputting section 84 can output and review defect information accumulated in the defect information accumulation section 83.

If the review results indicate the need for a re-inspection, defect position information is sent to the inspection control CPU via the shared memory 82, and only the part of interest is re-inspected.

Additionally, because it is possible to generate a database whereby defect information is stored in a database system 85, it is it possible in combination with an exposure simulator to perform classification, to analyze process problems based on past defect information, and to perform such functions as simulations of positioning between layers, thereby providing further enhanced inspection system capability.

A die-to-die inspection, whereby the same pattern disposed at different locations on one and the same reticle is described below.

Figure 6:
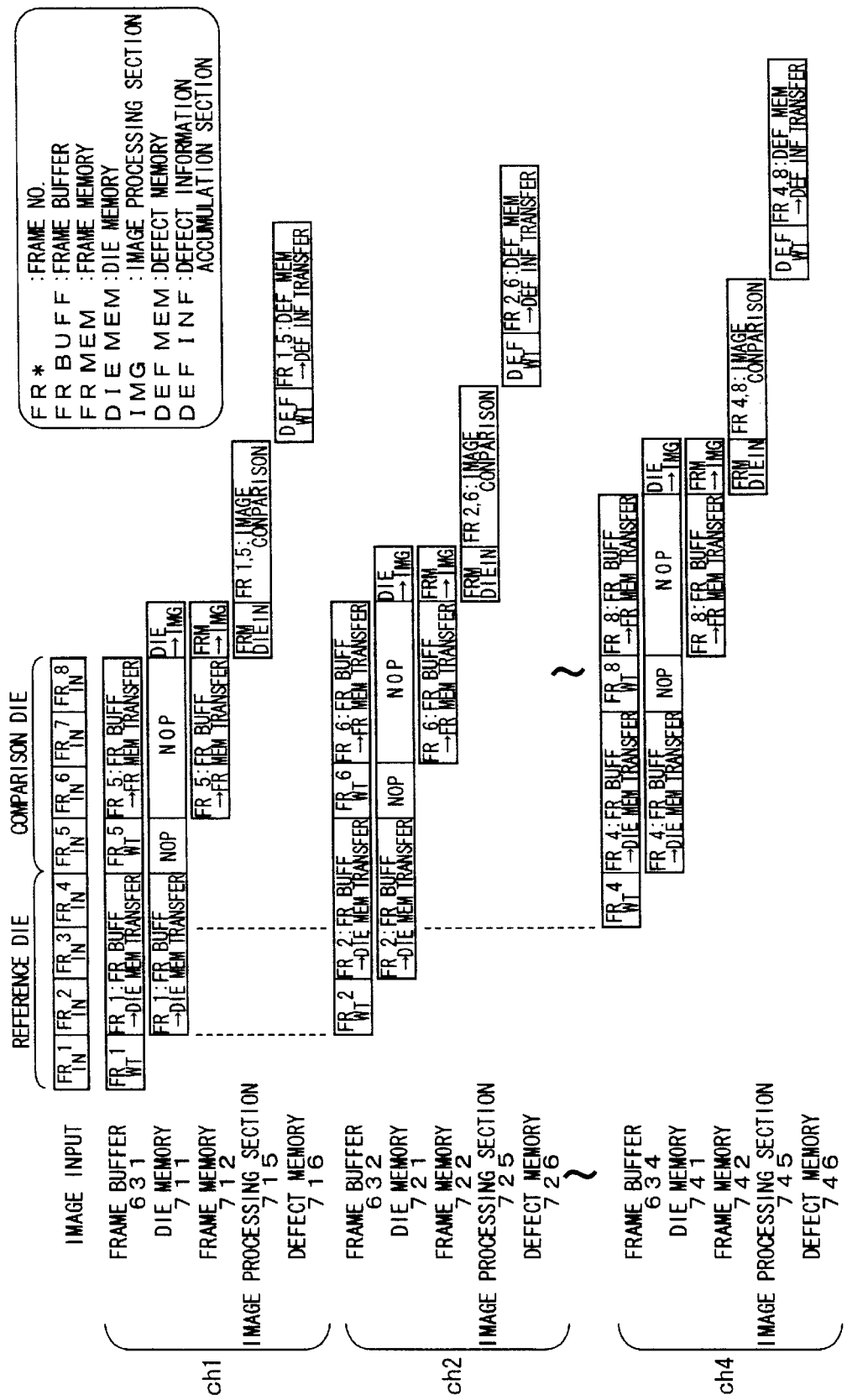
FIG. 6 is a timing diagram of inspection performed by the other example of a pattern inspection apparatus according to the present invention.

FIG. 5 illustrates the operation in a die-to-die inspection according to the present invention, and FIG. 6 is a timing diagram illustrating die-to-die inspection according to the present invention.

In a die-to-die inspection, an optical image of a reference die is acquired and accumulated in a DIE memory, after which when an optical image of a die to be compared is captured, a comparison is performed by extracting one frame at a time from the DIE memory so as to detect defects.

The inspection processing is processing whereby an inspection control CPU 14 calculates beforehand the overall number of frames to be handled as reference dies, that is, as comparison pattern images and the starting frame number for the comparison dies, these being transferred to each image comparison section via a shared memory.

In the conceptual drawing of FIG. 5, the overall number of reference die frames is 4, and the starting frame for the comparison die is 5.

When the inspection begins, similar to the case of the die-to-database inspection, the overall control CPU 21 sends a command to the stage controller 22 and the optical system controller 23, so as to start optical image acquisition.

After a detected image signal is input to the image input section 61 and a two-dimensional image is formed, control of the timing generator 62 is done to perform sequential divisions into frames, which are written into the frame buffers 631 to 634, and transferred to the image comparison sections.

Thereafter, the description continues for the case of the image comparison section 71, although the same processing is performed asynchronously by the other image comparison sections 72 to 74 as well.

The image processing section 715 reads from the shared memory 714 the overall number of frames in the reference die and the starting frame number of the comparison die, and enables the DIE memory 711, which is one of the reference pattern image information storage means, a frame that is transferred from the frame buffer 631 being sequentially written into the DIE memory 711, frames being accumulated until the total number of frames to be written is reached.

Next, if the starting frame number of the comparison die is encountered, the image processing section 715 enables the frame memory 712, and an optical image from the frame buffer 631 is accepted by the frame memory 712.

Next, the image processing section 715 extracts the first frame (FR1) from the DIE memory 711 as the reference frame, compares this with an optical image (FR5) of the comparison frame obtained from the frame memory 712, and performs a defect inspection.

In the case in which there is a defect detected, the image processing section 715 writes the defect information into the defect memory 716, and sends the defect information to the defect information accumulation section 83 of the review controller 8 in real time. In this case as well, because the route of writing the reference image data and inspection control information, which is from the shared memory 15 to the shared memory 714, is total independent from the route of outputting the defect information, form the defect memory 716 to the defect information accumulation section 83, it is possible to sent defect information without interrupting the inspection.

While the above-noted description was for the example of four image comparison sections, it will be understood that the present invention can be applied to the case in which there are a plurality of image comparison sections.

By adopting the technical constitution described above, the present invention achieves a number of effects.

Firstly, even when in the case in which a large number of defects are found in each inspection region or when performing real-time reviewing of defects during inspection because the route of accepting defect information is independent between the channels, it is possible to accept defect information without having to interrupt the inspection process. Furthermore, because no waiting time occurs, it is possible to shorten the overall time for inspection.

A second effect achieved by the present invention is that, because the review controller is independent from the inspection controller, it is possible to add sophisticated functions such as a database function or an exposure simulation function for operation during inspection, thereby improving the productivity of the apparatus.

What is claimed is:

1. A method for inspecting a pattern comprising:
   (1) dividing a pattern under inspection into a preestablished number of regions and sequentially acquiring, via an optical means, image information with regard to partial patterns under inspection in each region;
   (2) storing said image information with regard to said partial pattern under inspection acquired by said first step into a comparison pattern image information storage means provided in each of a pre-established plurality of image comparison sections, respectively;
   (3) in image processing means provided in each individual image comparison section, performing a comparison between said image information with regard to said partial patterns under inspection stored in said comparison pattern image information storage means and reference pattern image information corresponding to said partial pattern under inspection in said divided regions, which is stored beforehand in a reference pattern image information storage means provided in said image comparison sections;
   (4) in the case in which defect information exists with regard to a partial pattern under inspection, storing the defect information into a defect information storage means provided in a review controller; and
   (5) outputting said defect information with regard to partial patterns under inspection for a prescribed divided region stored in said defect information storage means in a prescribed format or at a prescribed time.

2. A method for pattern inspection according to claim 1, wherein said pre-established number of comparison sections is smaller than the prescribed number of divided region of said partial patterns under inspection.

3. A method for pattern inspection according to claim 1, wherein said reference pattern image information is a database of digital image data generated when said pattern is formed.

4. A method for pattern inspection according to claim 1, wherein said reference pattern image information is image information derived from a pattern having substantially the same shape as said pattern under inspection, and which is obtained from a reference pattern formed on the same pattern holding member as is formed the pattern under inspection.

5. A method for pattern inspection according to claim 4, wherein said reference pattern that provides said reference pattern image information is disposed near said inspection pattern of said pattern holding member.

6. A method for pattern inspection according to claim 5, wherein said reference pattern is a pattern detected as a pattern falling into a range of patterns under which said pattern can be seemed to be substantially similar to said partial pattern under inspection inspected in one inspection step in said pattern under inspection.

7. A method for pattern inspection according to claim 4, wherein a reference pattern detection operation is performed in advance with a prescribed amount of timing before an operation of detecting said corresponding partial pattern under inspection.

8. A method for pattern inspection according to claim 4, wherein said partial pattern under inspection is detected as a comparison image pattern.

9. A method for pattern inspection according to claim 1, wherein said reference pattern image information storage means minimally has stored therein either reference pattern image information from a database corresponding to a pattern under inspection selected from a digital image database, or reference pattern image information that is image data obtained via the optical means from the reference pattern held in the pattern holding member.

10. A method for pattern inspection according to claim 1, wherein of the calculation results obtained by the image processing sections provided in each one of said image comparison sections, image data indicating defects in a prescribed pattern under inspection is all sequentially stored into a defect information storing means provided in said review controller.

11. A method for pattern inspection according to claim 1, wherein said review controller outputs said defect information independently of any one of steps (1) to (4).

12. A method for pattern inspection according to claim 1, wherein image information stored in the comparison pattern image information storage means and reference pattern image information storage means in said image comparison section is overwritten by another image information at a prescribed timing.

13. A method for pattern inspection according to claim 1, wherein said pattern under inspection is divided into a prescribed number of inspection areas, and further wherein each one of said inspection areas is further divided into a plurality of divided regions, each forming a fine frame, and wherein said plurality of divided regions in one inspection area are sequentially scanned by an optical detection means so that said partial patterns under inspection are read, and at which time said reading is done so that a prescribed portion of said respective divided regions each being adjacently arranged to each other and which including an end part of the respective divided regions said end part of which being mutually connected to each other, are read out simultaneously in over-lapping manner.

14. A method for pattern inspection according to claim 1, wherein said review controller comprises a database system that minimally stores digital image data, pattern manufacturing process data, and past defect data, and outputs, along with the latest pattern defect information detection results, information appropriately related to processing of the latest pattern defect information.

15. A pattern inspection apparatus for detecting pattern defects of various kinds of patterns, comprising:
   a moving holding means for holding and moving in a prescribed direction a pattern holding member that holds a pattern under inspection;
   an optical means for generating pattern image data of a partial pattern under test from a pattern under test held by said moving holding means for every predetermined divided region of said pattern under inspection;
   a plurality of image comparison sections that compare said individual partial patterns under inspection of said pattern under inspection with prescribed reference pattern image information, and make a judgment as to whether or not a defect exists in said partial patterns under inspection, each of said image comparison sections comprising:
      a comparison pattern image information storage means which stores comparison pattern image data for a partial pattern under inspection corresponding to a specific inspection divided region,
      a reference pattern image information storage means which stores reference pattern image data corresponding to each of said partial patterns under inspection, and
      an image processing means that performs a comparison between said comparison pattern image data stored in said comparison pattern image information storage means and said reference pattern image data stored in said reference pattern image information storage means, and makes a judgment as to whether or not there is a defect in said pattern under inspection;
   a defect information accumulation means, which sequentially stores defect information in a prescribed partial pattern under inspection output by said image processing means in each of said image comparison sections; and
   a reviewing means, which outputs defect information with regard to each of said partial patterns under inspection stored in said defect information accumulation means with a prescribed format or at a prescribed time.

16. A pattern inspection apparatus according to claim 15, wherein said pattern under inspection is a reticule pattern.

17. A pattern inspection apparatus according to claim 15, wherein said pattern moving holding means is an XY stage.

18. A pattern inspection apparatus according to claim 15, wherein the number of said plurality of image comparison sections is smaller than the prescribed number of divided regions with regard to said partial pattern under inspection.

19. A pattern inspection apparatus according to claim 15, wherein said comparison pattern image information storage means stores pattern image information of a partial pattern under inspection disposed in each divided region and measured in real time as comparison image information.

20. A pattern inspection apparatus according to claim 15, wherein said reference pattern image information storage means includes data corresponding to said partial pattern under inspection selected from data that is digital image data generated when said pattern under inspection is formed.

21. A pattern inspection apparatus according to claim 15, wherein said reference pattern image information storage means includes patterns which is substantially identical to said pattern under inspection and which being pattern image information derived from a reference pattern formed on a holding means which is identical to said pattern holding means.

22. A pattern inspection apparatus according to claim 21, wherein said reference pattern that provides said reference pattern image information is disposed near said partial pattern under inspection in said pattern holding member.

23. A pattern inspection apparatus according to claim 22, wherein said reference pattern is a pattern detected as a pattern falling into a range of patterns under which said pattern can be seemed to be substantially similar to said partial pattern under inspection inspected in one inspection step in said pattern under inspection.

24. A pattern inspection apparatus according to claim 15, wherein an operation of detecting said reference pattern is performed in advance with a prescribed amount of timing before an operation of detecting said corresponding partial pattern under inspection.

25. A pattern inspection apparatus according to claim 15, wherein, of the calculation results obtained by the image processing sections provided in each one of the image comparison sections, image data indicating defects in said partial pattern under inspection is stored into defect information accumulation means provided in the review controller and connected separately to each image comparison section.

26. A pattern inspection apparatus according to claim 15, wherein said review controller further includes a database system into which is minimally stored digital image data, pattern manufacturing process data, and past defect judgment results data.

27. A pattern inspection apparatus according to claim 15, wherein said comparison pattern information storage means and said reference pattern image information storage means in said image comparison section are configured so as to be replaced by a comparison pattern image information or reference pattern image information corresponding to a different partial pattern under inspection disposed in a different divided region.

28. A pattern inspection apparatus according to claim 15, wherein said pattern under inspection is divided into a prescribed number of inspection areas, and further wherein each one of said inspection areas is further divided into a plurality of divided regions, each forming a fine frame, a plurality of said divided region in one inspection area being sequentially scanned by an optical detection means so that said partial patterns under inspection are read, at which time a read length for reading each one of adjacent divided regions by said optical detection means, is established at a length extending beyond an edge part of the divided region at which both divided regions being connected to each other so that there is a partial overlap between adjacent divided regions in this reading operation.

29. A pattern inspection apparatus according to claim 15, wherein said review controller and each said image comparison section is provided with a shared memory means having a mutually common function.

* * * * *